United States Patent
Fitts, Jr. et al.

(10) Patent No.: US 7,722,589 B2
(45) Date of Patent: May 25, 2010

(54) STRETCH ACTIVATED ARTICLE FOR DELIVERING VARIOUS COMPOSITIONS OR FUNCTIONAL ELEMENTS

(75) Inventors: James R. Fitts, Jr., Gainesville, GA (US); Janis W. Hughes, Alpharetta, GA (US); Bryon P. Day, Canton, GA (US); Ann L. McCormack, Cumming, GA (US); Wing-Chak Ng, Suwanee, GA (US); Varunesh Sharma, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1074 days.

(21) Appl. No.: 11/217,080

(22) Filed: Aug. 31, 2005

(65) Prior Publication Data
US 2007/0049894 A1    Mar. 1, 2007

(51) Int. Cl.
*A61F 13/15* (2006.01)

(52) U.S. Cl. .................. 604/385.22; 604/383; 604/387; 604/385.24; 604/385.16; 604/390; 604/391; 604/385.11

(58) Field of Classification Search ............ 604/385.22, 604/383.384, 385.24, 385.27, 385.16, 385.11, 604/385.03, 387, 390, 391, 383
See application file for complete search history.

(56) References Cited

U.S. PATENT DOCUMENTS

| | | | |
|---|---|---|---|
| 3,485,706 A | 12/1969 | Evans | |
| 3,655,501 A | 4/1972 | Tesch | |
| 3,855,046 A | 12/1974 | Hansen et al. | |
| 4,063,559 A | 12/1977 | Tritsch | |
| 4,600,620 A | 7/1986 | Lloyd et al. | |
| 4,603,069 A | 7/1986 | Haq et al. | |
| 4,753,231 A | 6/1988 | Lang et al. | |
| 4,797,310 A | 1/1989 | Barby et al. | |
| 4,969,970 A | 11/1990 | Suzuki et al. | |
| 5,068,941 A | 12/1991 | Dunn | |
| 5,348,153 A | 9/1994 | Cole | |
| 5,445,825 A | 8/1995 | Copelan et al. | |
| 5,524,764 A | 6/1996 | Kaufman et al. | |
| 5,741,564 A | 4/1998 | Gillberg-LaForce | |

(Continued)

FOREIGN PATENT DOCUMENTS

EP    0685586 A2    12/1995

(Continued)

OTHER PUBLICATIONS

PCT Search Report, Feb. 1, 2007.

*Primary Examiner*—Jacqueline F. Stephens
(74) *Attorney, Agent, or Firm*—Dority & Manning, P.A.

(57) ABSTRACT

A stretch activated disposable article, such as a wipe or mitt, includes an upper material layer, and a lower material layer joined to the upper material layer such that a space is defined between the material layers. A functional element, for example a fluid composition, is stored in the space between the upper and lower material layers and becomes functional upon being exposed through the upper material layer with use of the article. The upper material layer includes a plurality of materially weakened positions along the surface thereof that are configured to part or separate upon stretching of the upper material layer to expose the functional element through the upper material layer.

5 Claims, 5 Drawing Sheets

U.S. PATENT DOCUMENTS

| | | |
|---|---|---|
| 5,804,021 A | 9/1998 | Abuto et al. |
| 5,819,765 A | 10/1998 | Mittiga |
| 5,839,608 A | 11/1998 | Gillberg-LaForce |
| 5,873,868 A | 2/1999 | Nakahata |
| 5,901,419 A | 5/1999 | Widlund et al. |
| 6,262,331 B1 | 7/2001 | Nakahata et al. |
| 6,270,875 B1 | 8/2001 | Nissing |
| 6,336,763 B1 | 1/2002 | Losier et al. |
| 6,420,625 B1 | 7/2002 | Jones et al. |
| 6,503,855 B1 * | 1/2003 | Menzies et al. ............. 442/328 |
| 6,647,549 B2 | 11/2003 | McDevitt et al. |
| 6,716,498 B2 | 4/2004 | Curro et al. |
| 6,721,987 B2 | 4/2004 | McDevitt et al. |
| 6,808,791 B2 | 10/2004 | Curro et al. |
| 6,830,800 B2 | 12/2004 | Curro et al. |
| 6,863,960 B2 | 3/2005 | Curro et al. |
| 6,878,433 B2 | 4/2005 | Curro et al. |
| 6,884,494 B1 | 4/2005 | Curro et al. |
| 2002/0150431 A1 | 10/2002 | Ofosu-Asante et al. |
| 2003/0028985 A1 | 2/2003 | Prodoehl et al. |
| 2004/0109720 A1 | 6/2004 | Gruenbacher et al. |

FOREIGN PATENT DOCUMENTS

| | | |
|---|---|---|
| JP | 60190712 A | 9/1985 |
| JP | 63290819 A | 11/1988 |
| WO | 03000162 | 1/2003 |

* cited by examiner

STRETCH ACTIVATED ARTICLE FOR DELIVERING VARIOUS COMPOSITIONS OR FUNCTIONAL ELEMENTS

BACKGROUND OF THE INVENTION

Pre-moistened disposable wipes are known in the art for delivering various types of compositions, such as lotions, medications, cleaning agents, and so forth. These products are typically supplied in a rolled or stacked configuration within a container, with all of the wipes having been wetted with the desired composition prior to being loaded into the container. Refill packs of the pre-moistened wipes are often provided for subsequent insertion into the container, and are typically embodied as a sealed liquid impermeable package of the wipes.

Conventional pre-moistened wipe systems also generally require substantial and relatively expensive packaging to ensure that the wipes retain the fluid composition over prolonged periods of time prior to actual use of the individual wipes. Also, the user is required to grasp the wipe to remove it from the wipe container. This generally results in at least some of the composition being transferred to the user's hands, a consequence that is not desirable in all situations, particularly if the composition is a harsh cleaning agent or may stain or dye the user's skin. Also, it is often the situation that a relatively large container of the wipes must be transported and stored when only a single or few wipes are needed.

Another type of disposable product used to deliver a desired composition are tubular or mitt type structures that fit onto a user's finger(s) or hand. These devices are typically used for applying ointments, medications, alcohol, oral anesthetics, and the like, to various body parts, or may be utilized to remove various substances, such as makeup, or to clean body parts or other objects. The finger devices are sometimes referred to as "finger wipes" or "finger covers" and have proven particularly useful in the field of dental hygiene in that they provide a portable and efficient means for more frequent dental care, and as a cleaning device that can be easily used in public. In particular, a number of finger wipes have been developed that can be placed over a finger and wiped over the teeth and gums. These devices are typically small, portable, and disposable.

Examples of dental hygiene finger wipes are disclosed, for instance, in U.S. Pat. No. 6,721,987 to McDevitt, et al. and in U.S. Pat. No. 6,647,549 also to McDevitt, et al., which are incorporated herein by reference. An oral hygiene finger device is also described in U.S. Pat. No. 5,445,825 to Copelan et al. Finger-mounted dental wipes have been developed to contain an elastomeric material to help prevent the device from slipping or falling off the user's finger during cleaning. Examples of such teeth cleaning devices are disclosed in U.S. Pat. No. 5,068,941 to Dunn; U.S. Pat. No. 5,348,153 to Cole; U.S. Pat. No. 5,524,764 to Kaufman et al.; and PCT Publication No. WO 95/31154 to Mittiga et al.

Finger wipes that incorporate an integral additive or composition, such as an oral hygiene agent, lotion, cleaning agent, and the like, are a convenient and desirable product. However, it may be difficult to incorporate an adequate supply of the desired composition with conventional finger wipe constructions, or to ensure that the composition is not exposed or delivered prematurely. Consumers often resort to using multiple wipes to achieve a desired application of the composition, or apply an externally carried container of the composition, such as a small tube of toothpaste, to the finger wipe after initial use of the wipe.

Thus, the art is continuously seeking improved systems and methods to provide consumers with disposable articles, such as wipes, towels, finger wipes, and the like, that are supplied with any manner of desired composition prior to use. The present invention provides just such an improvement.

SUMMARY

Objects and advantages of the invention will be set forth below in the following description, or may be obvious from the description, or may be learned through practice of the invention.

In one aspect, the present disclosure is directed generally to disposable articles such as wipes, towels, finger wipes, mitts, and the like, that may be used to apply a composition or absorb a fluid during use. In this regard, a stretch activated article is provided having an upper material layer, and a lower material layer joined to the upper material layer along a seam such that a space is defined between the respective layers. The layers may be joined around a peripheral seam by any conventional method suited for the particular types of materials. A functional element is stored in the space between the upper and lower material layers and becomes "activated" or operational upon being exposed through the upper material layer with use of the article. Prior to use, the functional element is essentially sealed within the space between the material layers. The upper material layer includes a plurality of materially weakened positions along the surface thereof. These weakened positions are designed such that upon stretching the upper material layer, the weakened positions part, for example by bursting, tearing, rupturing, separating, or the like, to expose the functional element through the upper material layer.

The functional element may be any manner of composition depending on the intended use of the article. For example, the functional element may be a fluid composition that migrates through the parted weakened positions in the upper material layer, such as a lotion, cream, ointment, salve, liquid, and the like. The fluid composition may also be a powder or granular material that is capable of flowing out of the parted weakened positions. In the case of a liquid, the upper and lower material layers may be formed of a liquid impermeable material, such as a film, or a liquid impermeable laminate.

The functional element, particularly liquids or other fluid substances, may be stored in a free-flowing, uncontained state in the space between the material layers, or may be carried by an additional member, such as an absorbent structure disposed in the space between the upper and lower material layers. For example, the absorbent structure may be an absorbent web that has been saturated with the fluid composition.

The weakened positions may be defined as various structural changes to the upper material layer. For example, the weakened positions may be a plurality of relatively fine slits defined partially or completely through the upper material layer in any number of patterns. The slits remain essentially sealed until the upper material layer is stretched, whereupon the slits pull apart to expose the functional element. The upper material layer may be an elastomeric material such that upon release of the stretching force on the material, the slits close and essentially re-seal.

In an alternative embodiment, the upper material layer is non-elastomeric and the weakened positions undergo a generally permanent deformation upon being stretched. For example, the slits may pull apart and define permanent openings, or result in propagation of a tear or rupture in the material. The weakened positions may be defined by score lines that separate when the upper material layer is pulled or stretched. In still another embodiment, the weakened positions may be intentionally thinned positions in the material that rupture upon the material being stretched.

In another embodiment, the article may be designed to absorb liquids through the upper material layer. In this regard, the functional element may be an absorbent structure, such as an absorbent web, that absorbs liquid through the upper material layer in use of the article. This embodiment may be particularly well suited as a cleaning article, and the absorbent web may further include a cleaning agent that is released through the upper material layer. The absorbent web may include super absorbent particles (SAP) to enhance the absorptive capacity of the article.

In other embodiments, the article may include a back material layer that defines a pouch-like configuration with the lower material layer such that a user may slip the article onto their hand or finger(s). For example, the article may be a cleaning mitt, or a finger wipe used to polish or clean any manner of article. The upper material layer may be stretched upon the user donning the article to part the weakened positions and expose the functional element. In a particular embodiment, the article is a dental hygiene finger wipe and the functional element is an oral hygiene agent that is dispersed through the upper material layer upon donning the finger wipe. The upper material layer may include a textured outer layer, such as a textured nonwoven material, to aid in cleaning the user's teeth or gums.

In another aspect of the invention, the functional element is an attachment element. For example, the element may be an adhesive that migrates through the upper material layer upon use of the article. In an alternate embodiment, the functional element may include a web of conventional hook material, such as the micro hook material used with securing tabs in conventional disposable diapers and the like. In use, upon the upper material layer being stretched, the individual hooks extend through the parted weakened positions in the material. The article may thus be used as a securing mechanism between any two elements, such as a securement strap between two pieces of material. In this regard, the invention includes any manner of garment that utilizes such a securement article. For example, the invention includes disposable gowns, such as a surgical or patient gown, which uses the article to secure the gown relative to the user. The securement articles may be used as cuff straps or as a replacement for tie straps.

In still a further aspect, the invention encompasses any manner of absorbent article worn by a user to absorb bodily fluids, such as a diaper, training pant, swim pant, adult incontinent article, and the like, that uses an attachment structure according to the teachings of the present invention. For example, the attachment structure may be disposed along a waistband portion of an absorbent article, and include an adhesive composition that migrates out through the outer (upper) layer upon stretching the waistband. The adhesive may be formulated to releasably attach the waistband portion to the user's skin. In another embodiment, the attachment structure may include attachment tabs or strips disposed on opposite lateral sides of the absorbent article with a web of hook material having hooks that extend through the parted weakened positions of the outer material layer upon stretching the attachment strips. As in various commercial disposable diapers, the hooks attach to a complimentary pad of material to secure the absorbent article on the user.

In an alternate embodiment, the absorbent article is a feminine hygiene article, such as a panty liner or pad, and the attachment structure is disposed on the outside of the baffle so as to attach the feminine hygiene article to the user's undergarment. For example, the attachment element may be a fluid adhesive composition that migrates through the parted weakened positions in the outer material layer upon stretching the absorbent article prior to pressing the absorbent article to the user's undergarment. In an alternate embodiment, the attachment element comprises a web of hook material having individual hooks that extend through the parted weakened positions in the outer material layer and attach directly to the user's undergarment.

Various features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Repeat use of reference characters in the present specification and drawings is intended to represent the same or analogous features or elements of the invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

Embodiments of various stretch activated articles in accordance with the invention are illustrated generally as the articles 10 in the figures. In general, each of the articles 10 includes an upper layer 12, a lower layer 14, and a space 16 defined between the upper and lower layers. The upper and lower layers may be attached together along a perimeter seam 15 by any conventional method that is compatible with the particular materials, such as stitching, adhesives, bonding, welding, and so forth. A functional element 20 is stored in the space 16 between the upper material layer 12 and lower material layer 14. The functional element 20 becomes activated or otherwise operational upon being exposed through the upper material layer 12 in use of the article 10. Prior to use, the functional element 20 is essentially sealed within the space 16 between the material layers 12, 14.

The upper material layer 12 includes a plurality of materially weakened positions, generally 22, defined in any desired pattern along the surface of the upper material layer 12. These weakened positions 22 are designed such that upon stretching the upper material layer 12, the weakened positions part or separate, for example by bursting, tearing, rupturing, or the like, to expose the functional element 20 through the upper material layer 12.

The functional element 20 may be any manner of composition or device depending on the intended use of the articles 10. For example, the functional element 20 may be a fluid composition that migrates through the parted weakened positions 22 in the upper material layer 12 upon pressure or other actuating force being applied to the article 10. The fluid composition can be any manner of lotion, cream, ointment, salve, liquid, and the like. For embodiments wherein the articles 10 are used for cleaning or scrubbing purposes, the functional element 20 may be, for example, a fluid cleaning agent, or the like. The fluid composition 30 may also be in a powder or granular form that is capable of flowing out of the parted weakened positions 22 from the space between the cover layer 12 and lower layer 14.

The functional element 20, particularly liquids or other fluid compositions, may be stored in a free-flowing or uncontained state within the space 16 between the upper layer 12 and lower layer 14. In this embodiment, both of the layers 12, and 14, may be formed from any manner of suitable liquid impermeable material, such as a film, a liquid impermeable laminate, and so forth. Suitable materials are discussed in greater detail below.

In an alternate embodiment, the functional element 20 may include an additional element contained within the space 16 between the layers 12, 14. For example, such additional structure may include an absorbent web, sponge, or like structure. A fluid composition 30 may be contained by the absorbent structure. This configuration may give a more controlled release of the fluid composition 30 through the upper material layer 12, particularly for highly viscous fluid compositions 30.

Figure 1:
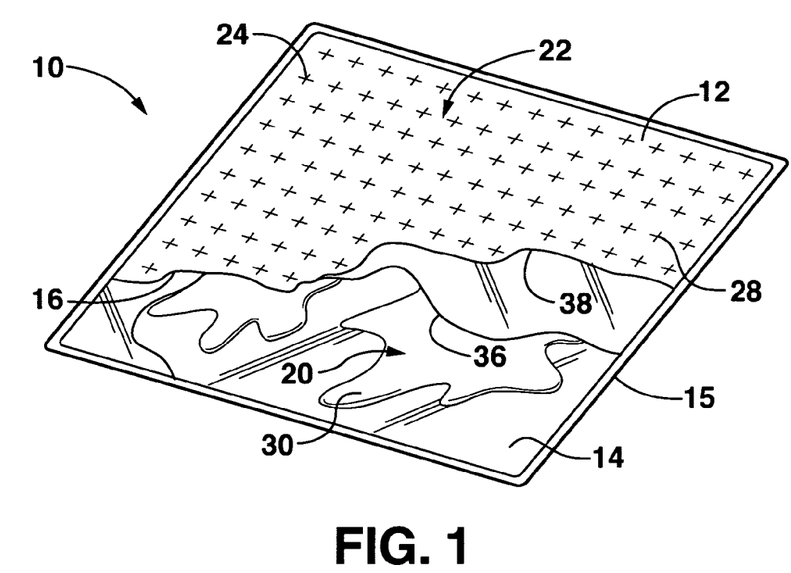
FIG. 1 is a perspective and partial cut-away view of an article according to one embodiment of the present invention embodied as a pad or wipe.
Figure 2:
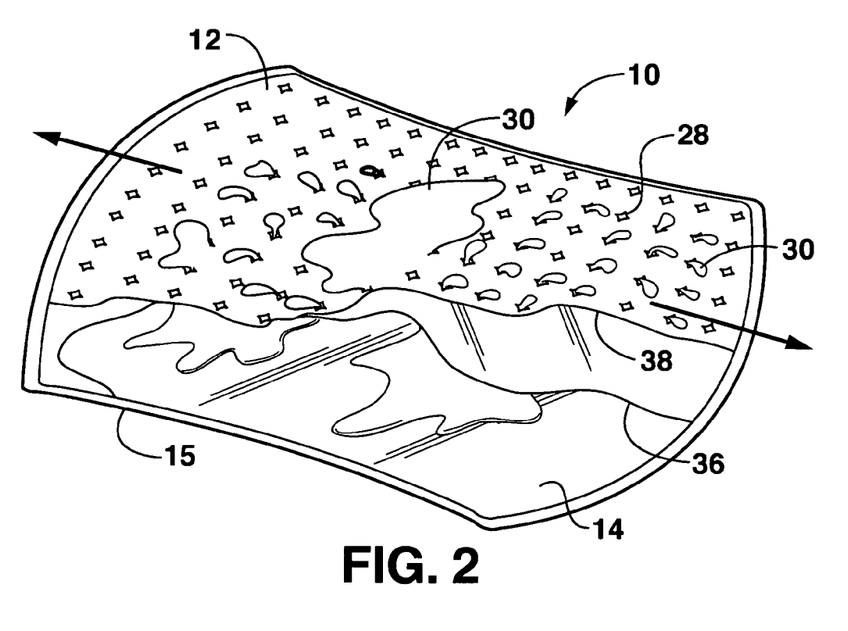
FIG. 2 is a perspective and partial cut-away view of the article in FIG. 1 shown in a stretched state.

In FIGS. 1 and 2, the article 10 is illustrated as a pad, such as a cleaning pad, wipe, or other similar device. In this embodiment, the materially weakened positions 22 in the upper cover layer 12 are defined by a pattern of thinned portions 28 in the cover layer material. These thinned portions 28 may be defined by various means depending on the type of material selected for the cover material layer 12. For example, the thinned portions 28 may be mechanically defined, such as by etching, stretching, or the like. The thinned portions 28 may be thermally or chemically defined in the material 12.

Referring to FIG. 2, upon stretching the article 10 such that the upper material layer 12 is stretched in at least one direction, the thinned portions 28 will rupture or tear and create flow holes through the upper material layer 12 through which the fluid composition 30 will migrate, as generally illustrated in FIG. 2. In this particular embodiment, the upper material layer 12 is a liquid impermeable material and is formed, for instance, of a laminate of a nonwoven material 38 and a film 36. Such laminate structures are well known to those skilled in the art and need not be described in detail herein. The lower material layer 14 may be a similar laminate construction, a film, or other suitable liquid impermeable material.

Figure 3:
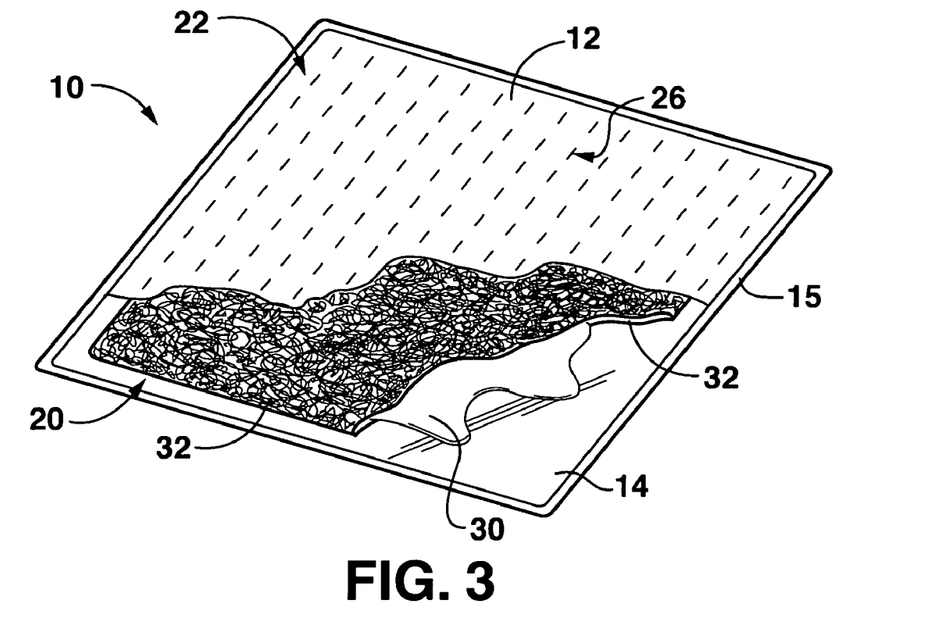
FIG. 3 is a perspective and partial cut-away view of an alternate pad embodiment according to the invention.

In the embodiment of FIG. 3, the article 10 is a pad and the weakened portions in the upper material layer 12 are defined by a series of relatively fine slits 26. These slits 26 may be defined completely through the upper material layer 12, or partially through the material. This may depend on the stiffness of the material layer 12, type of functional element 20, and so forth. For example, in the embodiment wherein the functional element is a highly viscous fluid composition 30, it may not be acceptable for the slits 26 to be defined completely through the material. However, in an embodiment wherein the fluid composition is a granular or powder material, then slits 26 defined completely through the material 12 may be acceptable. In either case, the slits 26 define a score line along which the material 12 tears or separates upon the material 12 being stretched.

In the embodiment of FIG. 3, the functional element 20 includes an absorbent web 32 that may be essentially saturated with the fluid composition 30. To release the composition 30, the article 10, and thus the absorbent web 32, is squeezed or otherwise subjected to pressure after the upper material layer 12 has been stretched. This particular configuration allows for a more controlled release of the fluid composition 30 through the upper material layer 12.

The embodiment of FIG. 3 may be particularly useful as a cleaning article wherein the fluid composition 30 is any manner of cleaning agent. The cleaning agent 30 is released from the article 10, but may be subsequently reabsorbed into the absorbent article 32, as well as any other liquid. Thus, the article 10 in this embodiment also functions as an overall absorbent article, such as an absorbent sponge, wipe, and the like.

Still referring to FIG. 3, it should be appreciated that the functional element 20 may constitute the absorbent web 32 alone. Thus, the functional element 20 in this case absorbs an external liquid or fluid composition through the material layer 12 after the material has been stretched. To enhance absorption of the absorbent structure 32, super absorbent particles (SAP) may be included with the absorbent structure 32, as is generally known in the art.

Figure 4:
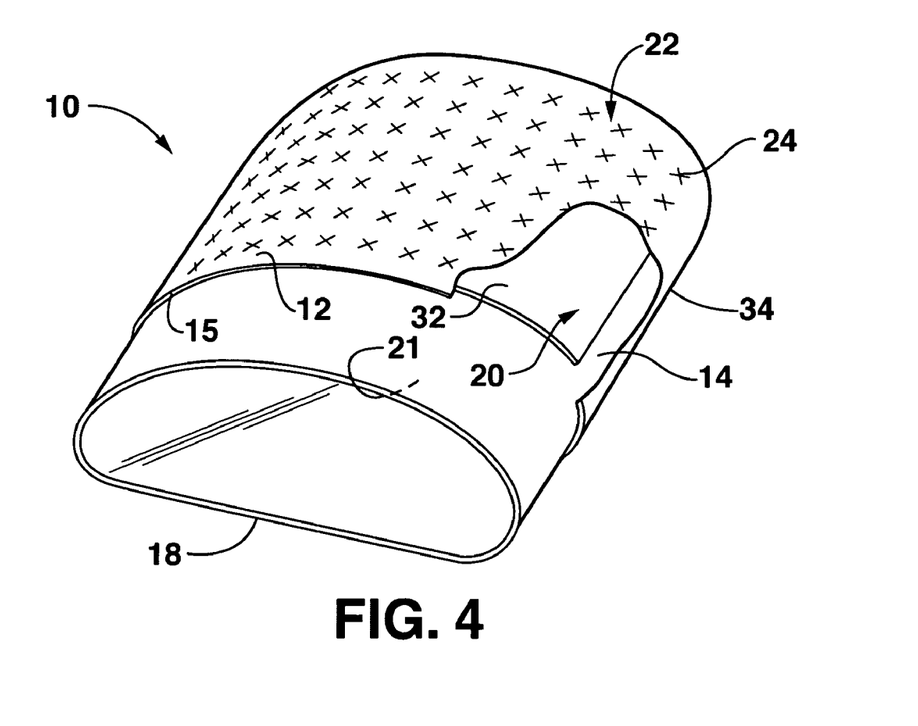
FIG. 4 is a perspective and partial cut-away view of a cleaning mitt embodiment in accordance with the invention.

In FIG. 4, the article 10 is configured as a pouch or mitt structure 34 that includes an additional layer 18 defining an internal space 21 between the layer 18 and lower layer 14. The structure is designed so that a user may insert their hand or multiple fingers within the internal space 21 in use of the article. In this particular embodiment, the functional element 20 is an absorbent structure 32 that may or may not include a fluid composition 30. The weakened positions 22 defined in the upper material layer 12 are a series of cross-slits 24 that may be defined completely through the material. The mitt 34 may be stretched by the user prior to donning, or the material layer 12 may be stretched by the user as their hand or fingers are inserted into the structure in order to open the slits 24 and expose the absorbent structure 32.

Figure 5:
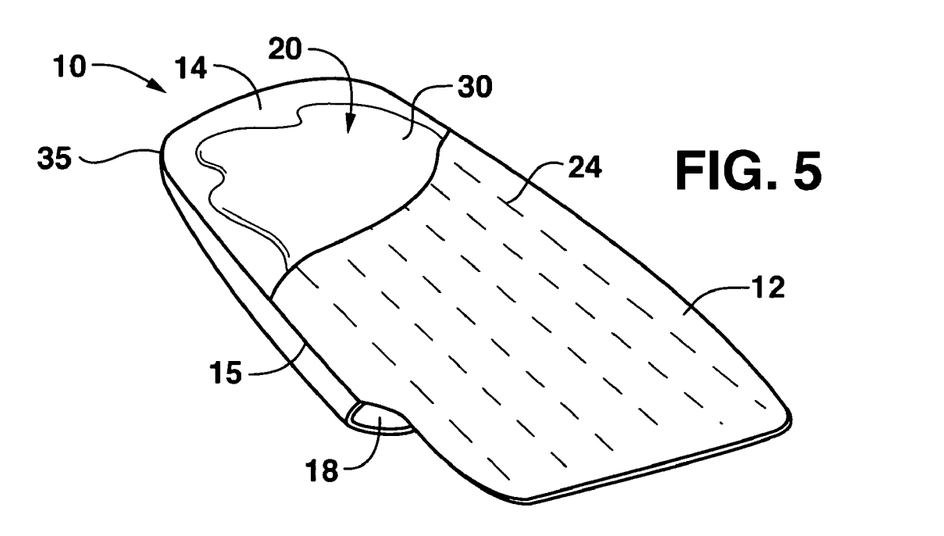
FIG. 5 is a perspective and partial cut-away view of a finger wipe embodiment according to the invention.
Figure 6:
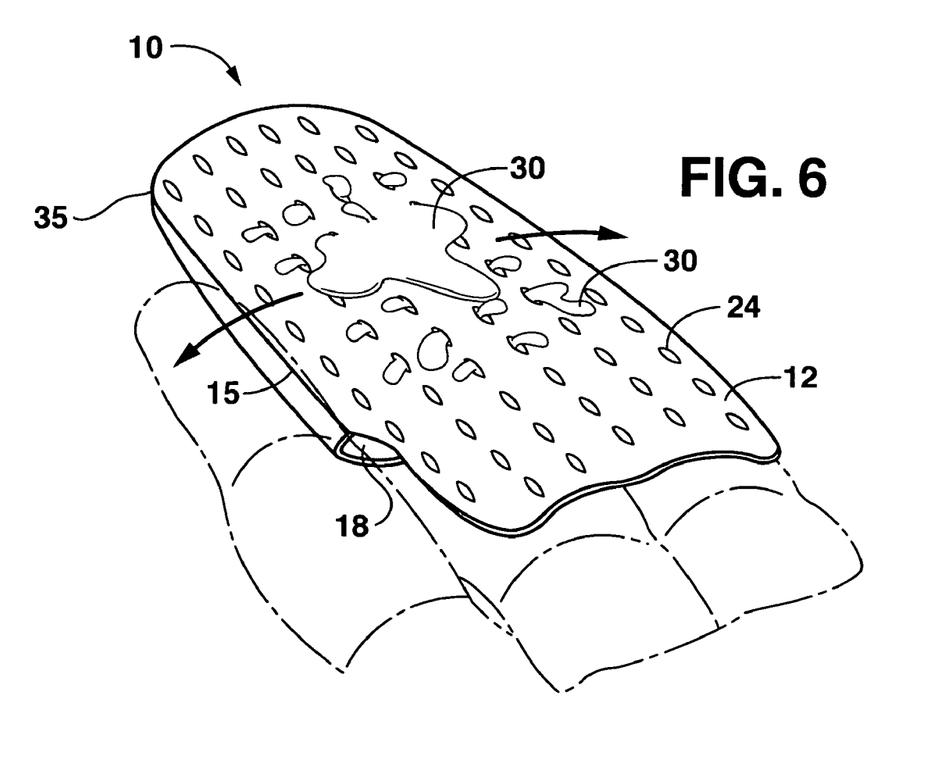
FIG. 6 is a perspective and partial cut-away view of an alternate embodiment of a finger wipe embodiment according to the invention.

FIGS. 5 and 6 illustrate an alternate embodiment of an article 10 as a finger wipe 35 designed to slide onto one or more of a user's fingers. The wipe 35 may be used to apply any manner of cleaning agent, polish, or the like to any type of article, body part, and so forth. In a particularly useful embodiment, the finger wipe 35 is configured as a dental hygiene finger wipe and the functional element 20 is an oral hygiene agent, such as toothpaste, and so forth. In this particular embodiment, the upper material layer 12 includes a series of spaced slits 24 that individually open when the material 12 is stretched, as illustrated in FIG. 6. This stretching may occur simply by donning the finger wipe 35, as illustrated in FIG. 6. Once the slits 24 have opened, the fluid composition 30 is free to migrate through the material layer 12. The material layer 12 may include a textured outer surface, such as a textured nonwoven material, to aid in cleaning the user's teeth, gums, and so forth. Suitable textured materials are described in greater detail below.

In still other embodiments, the functional element 20 may be an attachment element. For example, the functional element 20 may be an adhesive fluid composition that migrates through the upper material layer 12 upon use of the article 10. The adhesive may be applied to any manner of external objects, or may be used to attach the article 10 to another object.

Figure 7:
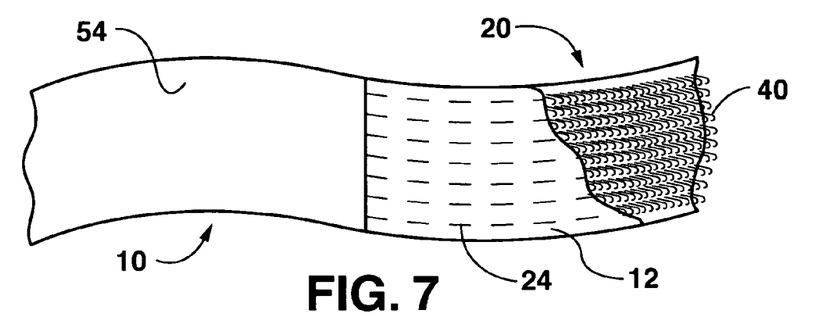
FIG. 7 is a perspective and partial cut-away view of a strap securement device article in accordance with the invention.

In the embodiment of FIG. 7, the article 10 is illustrated as a securement device, such as a strap 54 that may be used in any conventional use of securement straps, ties, hold-down devices, and so forth. In this particular embodiment, the functional element 20 is defined by a web of hook material, such as conventional microhook material used in various commercial absorbent articles such as diapers, training pants, and the like. The hook material includes individual hooks 40 that will protrude through the slits 24 defined in the material layer 12 in use of the strap 54.

Figure 8:
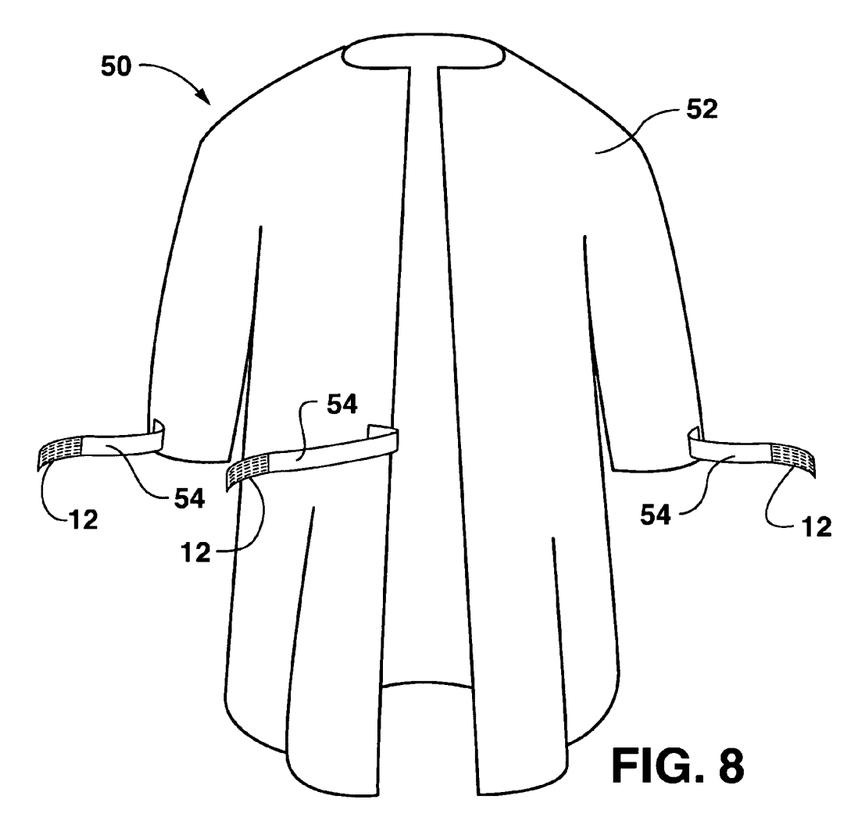
FIG. 8 is a perspective view of a garment incorporating strap securement devices shown in FIG. 7.

The strap device 54 illustrated in FIG. 7 may be incorporated with any manner of garment that utilizes a securement strap or tie. For example, referring to FIG. 8, a conventional surgical or patient gown 52 is illustrated as incorporating three of the securement straps 54. A strap 54 is supplied at each cuff of the gown, and another strap 54 is utilized as a tie across the back of the gown. Once the straps are pulled, the material layer 12 separates at the weakened positions and the hooks will extend through the material. The gown material may be a nonwoven material such that the hooks will attach directly to the gown material. In an alternate embodiment, a complimenting loop material may be provided for attachment of the hook material.

The strap device 54 may also be incorporated into any manner of bandage or wound care product to secure the product relative to the user.

Any manner of conventional absorbent article utilizing the novel aspects of the invention are contemplated. For example, any manner of diaper, training paint, swim pant, adult incontinence article, and the like, may incorporate aspects of the present invention. For example, referring to FIG. 9, a typical absorbent article 58 is illustrated as a disposable diaper 84 having a cover layer 60, baffle layer 62, and absorbent structure 64 disposed between the cover 60 and baffle 62, as is generally known in the art. An attachment structure 66 may be provided along the waistband portion 78 of the diaper 84. Referring to the center waistband portion 78, the attachment structure 66 may include an elastomeric outer material layer 68 having weakened portions 76 defined therein. A skin-friendly adhesive fluid composition may be contained within the attachment structure 66 below the outer material layer 68. Upon donning the diaper, the waistband portion 78, and thus the outer material layer 68, are stretched such that the weakened portions 76 part and the adhesive fluid composition migrates through the material layer 68. The adhesive fluid composition may be used to attach the waistband of the diaper 84 directly to the user's skin, a clothing article, or the like.

Figure 9:
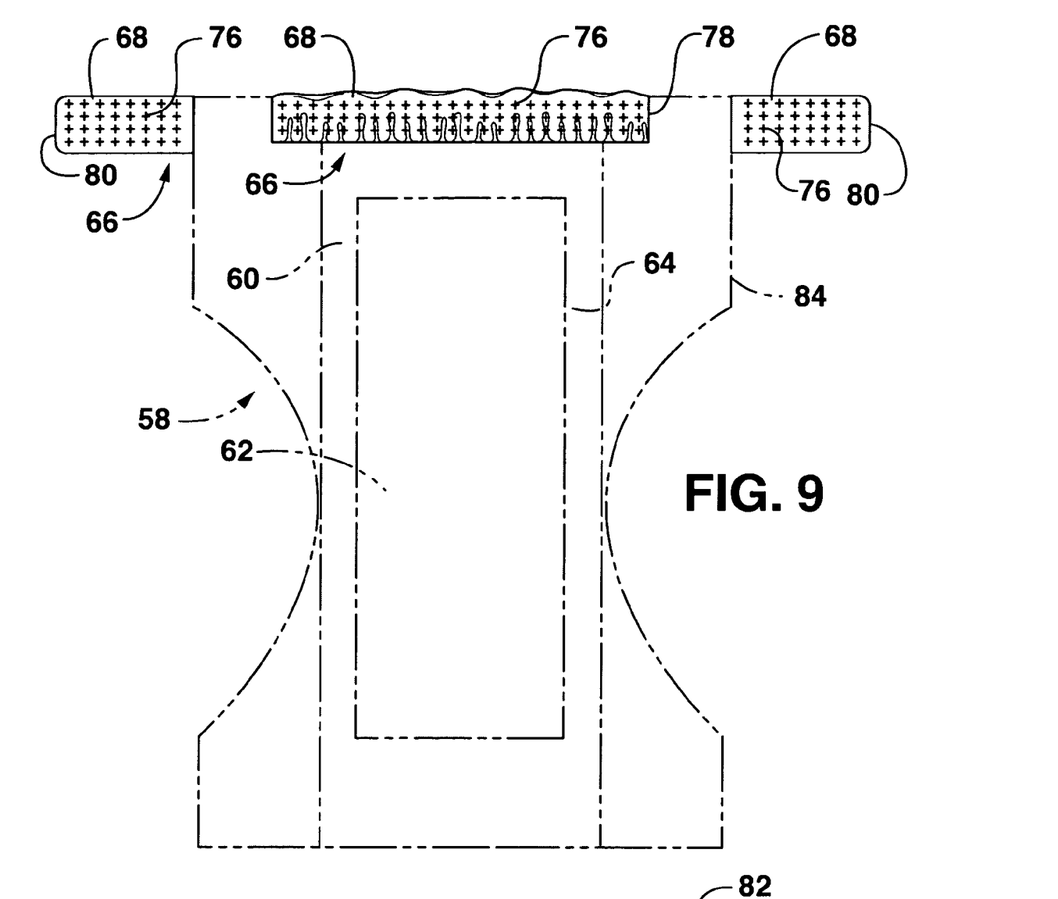
FIG. 9 is a partial perspective and plan view of a disposable article incorporating attachment structure devices in accordance with the invention.

Still referring to FIG. 9, the diaper 84 includes attachment tabs 80 at the lateral outboard edges, as is generally known in the art. These tabs 80 may incorporate structures similar to the strap embodiments of FIGS. 7 and 8 wherein microhook material is disposed below the outer material layer 68 and is exposed through the weakened position 76 upon the tabs 80 being stretched to don the diaper 84. The microhook material may attach directly to another nonwoven material portion of the diaper 84, as with any number of conventional diaper configurations.

Figure 10:
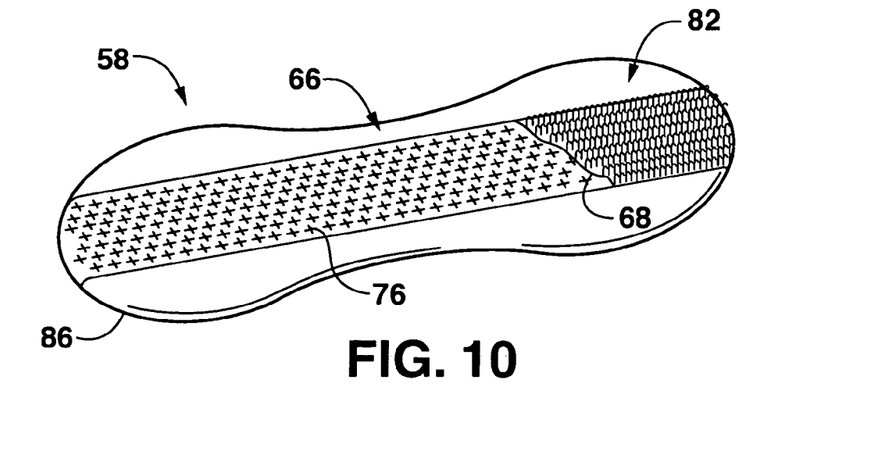
FIG. 10 is a perspective and partial cut-away view of a feminine hygiene article incorporating attachment structure in accordance with the invention.

FIG. 10 illustrates the absorbent article 58 as a feminine hygiene product, particularly a pantyliner 86. Attachment structure 66 is provided along the baffle material layer 62 and includes hook material 82 having individual hooks that will extend through the weakened position 76 in the outer material layer 68 upon the user stretching the article 58 prior to use. The hook material may attach directly to the user's undergarment. In an alternate embodiment, the functional element could be a fluid adhesive composition that is used to attach the article 58 to the user's undergarment.

In any of the embodiments, the upper material layer 12 may be an elastomeric material and the weakened positions may be relatively fine slits or cuts defined through the material. With this configuration, the upper material layer is stretched such that the slits pull apart and open, such as with the embodiment illustrated in FIGS. 5 and 6. Upon release of the stretching force on the material 12, the slits 24 will close and essentially seal. In alternate embodiments, the upper material layer 12 is a generally non-elastomeric material and the weakened positions undergo a generally permanent deformation upon being stretched. For example, slits 24 may pull apart and define permanent openings, or result in propagation of a tear or rupture in the material, such as along a perforation line 26 illustrated in FIG. 3.

Non-limiting examples of suitable materials that may be used in articles made in accordance with the invention are described in greater detail below.

Any one or all of the upper material layer 12, lower material layer 14, and backing layer 18 used in articles 10 according to the invention may include a base web of one or more layers of fibrous materials used in the art for making wipes. For example, the layers may include a liquid absorbent material or a non-absorbent material. When comprising a liquid absorbent material, the base webs may comprise any suitable fabric material, such as a woven fabric, a nonwoven fabric, or a knitted fabric.

In one embodiment, the base web comprises a spunbond web, a coform web, a tissue web, a meltblown web, a bonded carded web, and laminates thereof. A nonwoven material can be made from various fibers, such as synthetic or natural fibers. For instance, in one embodiment, synthetic fibers, such as fibers made from thermoplastic polymers, can be used to construct the cover layer of the present invention. For example, suitable fibers could include melt-spun filaments, staple fibers, melt-spun multi-component filaments, and the like. These synthetic fibers or filaments used in making the nonwoven material may have any suitable morphology and may include hollow or solid, straight or crimped, single component, conjugate or biconstituent fibers or filaments, and blends or mixtures of such fibers and/or filaments, as are well known in the art.

The synthetic fibers used in the present invention may be formed from a variety of thermoplastic polymers where the term "thermoplastic polymer" refers to a long chain polymer that repeatedly softens when exposed to heat and substantially returns to its original state when cooled to ambient temperature. As used herein, the term "polymer" generally includes, but is not limited to, homopolymers, copolymers, such as for example, block, graft, random, and alternating copolymers, terpolymers, etc., and blends and modifications thereof.

Synthetic fibers added to the nonwoven web can also include staple fibers that can be added to increase the strength, bulk, softness and smoothness of the base sheet. Staple fibers can include, for instance, various polyolefin fibers, polyester fibers, nylon fibers, polyvinyl acetate fibers, cotton fibers, rayon fibers, non-woody plant fibers, and mixtures thereof.

Besides, or in addition to, synthetic fibers, pulp fibers can also be used in the various material layers. The pulp fibers used in forming the cover layer may be soft wood fibers having an average fiber length of greater than 1 mm, and particularly from about 2 to 5 mm based on a length weighted average. Such fibers can include northern softwood kraft fibers, redwood fibers, and pine fibers. Secondary fibers obtained from recycled materials may also be used. In addition, hardwood pulp fibers, such as eucalyptus fibers, or thermomechanical pulp can also be utilized in the present invention.

In some embodiments of the present invention, the base web can include a hydraulically entangled web (or hydroentangled). Hydroentangled webs, which are also known as spunlace webs, refer to webs that have been subjected to columnar jets of a fluid that cause the fibers in the web to entangle. For example, in one embodiment, the cover layer can comprise HYDROKNIT®, a nonwoven composite fabric that contains 70% by weight pulp fibers that are hydraulically entangled into a continuous filament material. HYDROKNIT® material is commercially available from Kimberly-Clark Corporation of Neenah, Wis. Hydraulic entangling may be accomplished utilizing conventional hydraulic entangling equipment such as may be found in, for example, U.S. Pat. No. 3,485,706 to Evans or U.S. Pat. No. 5,389,202 to Everhart, et al., the disclosures of which are hereby incorporated by reference.

In one embodiment, the base web may comprise a laminate containing two or more webs. For instance, the web may comprise a spunbonded/meltblown/spunbonded laminate, a spunbonded/meltblown laminate and the like.

For nonwoven webs containing substantial amounts of synthetic fibers, the webs may be bonded or otherwise consolidated in order to improve the strength of the web. Various methods may be utilized in bonding webs of the present invention. Such methods include through air bonding and thermal point bonding as described in U.S. Pat. No. 3,855,046 to Hansen, et al. which is incorporated herein by reference. In addition, other conventional means of bonding, such as oven bonding, ultrasonic bonding, hydroentangling, or combinations of such techniques, may be utilized in certain instances.

In one embodiment, thermal point bonding is used which bonds the fibers together according to a pattern. In general, the bonding areas for thermal point bonding, whether pattern unbonded or pattern bonded fabrics, can be in the range of 50% total bond area or less. More specifically, the bond areas of the present inventive webs can be in the range of from about 60% to about 10% total bond area.

When the finger wipe or mitt embodiments of the present invention are used to scrub surfaces or in dental applications, the outer material layer may include a texturized surface. When used in dental applications, for instance, the texturized surface can facilitate removal of residue and film from the teeth and gums. The manner in which a texturized surface is formed on a nonwoven web for use in the present invention can vary depending upon the particular application of the desired result. The panel sections may be made from a nonwoven web that has been thermally point unbonded to form a plurality of tufts. As used herein, a substrate that has been "thermally point unbonded" refers to a substrate that includes raised unbonded areas or lightly bonded areas that are surrounded by bonded regions. For example, as shown in the figures, bumps or tufts are the unbonded or lightly bonded areas that form raised projections off the surface of the nonwoven web to provide the necessary texture.

The material used for the point unbonding process can vary depending upon the particular application. For instance, the material can be a single layer or can include multiple layers of material. For most applications, the total basis weight of the material should be at least 1 osy, and particularly from about 3 osy to about 9 osy. Higher basis weights are needed in order to produce tufts with an appropriate height.

Besides point unbonded materials, there are many other methods for creating texturized surfaces on base webs and many other texturized materials can be utilized.

Examples of known nonwoven, texturized materials, include rush transfer materials, flocked materials, wire-formed nonwovens, and the like. Moreover, through-air bonded fibers, such as through-air bonded bicomponent spunbond, or point unbonded materials, such as point unbonded spunbond fibers, can be incorporated into the base web to provide texture to the wipe.

Textured webs having projections from about 0.1 mm to about 25 mm, such as pinform meltblown or wireform meltblown, can also be utilized in a base web of the present invention. Still another example of suitable materials for a texturized base web includes textured coform materials. In general, "coform" means a process in which at least one meltblown diehead is arranged near a chute through which other materials are added to the web while it forms. Such other materials can include, for example, pulp, superabsorbent particles, or cellulose or staple fibers. Coform processes are described in U.S. Pat. No. 4,818,464 to Lau and U.S. Pat. No. 4,100,324 to Anderson, et al. Webs produced by the coform process are generally referred to as coform materials.

In one embodiment, the texturized material can be a loop material. As used herein, a loop material refers to a material that has a surface that is at least partially covered by looped bristles that can vary in height and stiffness depending upon the particular application. Further, the looped bristles can be sparsely spaced apart or can be densely packed together. The loop material can be made in a number of different ways. For example, the loop can be a woven fabric or a knitted fabric. In one embodiment, the loop material is made by needle punching loops into a substrate. In other embodiments, the loop material can be formed through a hydroentangling process or can be molded, such as through an injection molding process. Of course, any other suitable technique known in the art for producing looped bristles can also be used.

In one particular embodiment of the present invention, the loop material used in the finger wipe is a loop material commonly used in hook and loop fasteners. For example, VELCRO loops No. 002 made by VELCRO, USA, Inc. can be used. This material is made with nylon loops. In an alternative embodiment, the looped fastener material can be elastic. Elastic woven loop materials include VELSTRETCH Tape 9999 and MEDFLEX Tape 9399, both marketed by VELCRO, USA, Inc.

As mentioned, any one or combination of the material layers may be liquid impermeable, particularly if the functional element is a fluid composition. The liquid impermeable material may be separate from an adjacent base web, or may be a component of the base web. The liquid impermeable layer(s) can be made from liquid-impermeable plastic films, such as polyethylene and polypropylene films. Generally, such plastic films are impermeable to gases and water vapor, as well as liquids. In some embodiments, breathable, liquid-impermeable barriers are desired. As used herein, the term "breathable" means that the barrier or film is pervious to water vapor and gases. In other words, "breathable barriers"

and "breathable films" allow water vapor and gases to pass therethrough, but not necessarily liquids.

For instance some suitable breathable, liquid-impermeable barriers can include barriers such as disclosed in U.S. Pat. No. 4,828,556 to Braun, et al., which is incorporated herein in its entirety by reference. The breathable barrier of Braun, et al. is a multilayered, clothlike barrier comprised of at least three layers. The first layer is a porous nonwoven web; the second layer, which is joined to one side of the first layer, comprises a continuous film of PVOH; and the third layer, which is joined to either the second layer or the other side of the first layer not joined with the second layer, comprises another porous nonwoven web. The second layer continuous film of PVOH is not microporous, meaning that it is substantially free of voids that connect the upper and lower surfaces of the film.

In other cases, various films can be constructed with micropores therein to provide breathability. The micropores form what is often referred to as tortuous pathways through the film. Liquid contacting one side of the film does not have a direct passage through the film. Instead, a network of microporous channels in the film prevents water from passing, but allows water vapor to pass.

In some instances, the breathable, liquid-impermeable barriers are made from polymer films that contain any suitable substance, such as calcium carbonate. The films are made breathable by stretching the filled films to create the microporous passageways as the polymer breaks away from the calcium carbonate during stretching. In some embodiments, the breathable film layers can be used in thicknesses of from about 0.01 mils to about 5 mils, and in other embodiments, from about 0.01 mils to about 1.0 mils.

An example of a breathable, yet fluid penetration-resistant material is described in U.S. Pat. No. 5,591,510 to Junker. et al., which is incorporated herein by reference. The fabric material described in Junker, et al. contains a breathable outer layer of paper stock and a layer of breathable, fluid-resistant nonwoven material. The fabric also includes a thermoplastic film having a plurality of perforations which allow the film to be breathable while resisting direct flow of liquid therethrough.

In addition to the films mentioned above, various other breathable films can be utilized in the present invention. One type of film that may be used is a nonporous, continuous film, which, because of its molecular structure, is capable of forming a vapor-permeable barrier. Among the various polymeric films which fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. It is believed that films made from such polymers solubilize water molecules and allow transportation of those molecules from one surface of the film to the other. Accordingly, such films may be sufficiently continuous, i.e., nonporous, to make them liquid-impermeable but still allow for vapor permeability.

Still, other breathable, liquid-impermeable barriers that can be used in the present invention are disclosed in U.S. patent application Ser. No. 08/928,787 entitled "Breathable, Liquid-Impermeable, Apertured Film/Nonwoven Laminate and Process for Making the Same", which is incorporated herein in its entirety by reference. For example, breathable films and/or apertured films can be utilized in the present invention. Such films can be made within a laminate structure. In one embodiment, a breathable, liquid-impermeable, apertured film/nonwoven laminate material can be formed from a nonwoven layer, an apertured film layer, and a breathable film layer. The layers may be arranged so that the apertured film layer or the breathable film layer is attached to the nonwoven layer.

For instance, in one embodiment, an apertured film can be used in the present invention that is made from any thermoplastic film, including polyethylene, polypropylene, copolymers of polypropylene or polyethylene, or calcium carbonate-filled films. The particular aperturing techniques utilized to obtain the apertured film layer may be varied. The film may be formed as an apertured film or may be formed as a continuous, non-apertured film and then subjected to a mechanical aperturing process.

Liquid impermeable layers, as described above, can be used alone or incorporated into a laminate when used to construct various components of articles in accordance with the present invention. When incorporated into a laminate, the laminate can include various nonwoven webs in combination with the liquid impermeable layer. For instance, liquid impermeable laminates can be formed from many processes, such as, meltblowing processes, spunbonding processes, coforming processes, spunbonding/meltblowing/spunbonding processes (SMS), spunbonding/meltblown processes (SM), and bonded carded web processes. For instance, in one embodiment, the nonwoven layer of a laminate liquid impermeable layer of the present invention is a spunbond/meltblown/spunbond (SMS) and/or spunbond/meltblown (SM) material. An SMS material is described in U.S. Pat. No. 4,041,203 to Brock, et al. which is incorporated herein in its entirety by reference. Other SMS products and processes are described for example in U.S. Pat. No. 5,464,688 to Timmons, et al., U.S. Pat. No. 5,169,706 to Collier, et al. and U.S. Pat. No. 4,766,029 to Brock, et al., all of which are also incorporated herein in their entireties by reference. Generally, an SMS material will contain a meltblown web sandwiched between two exterior spunbond webs. Such SMS laminates are available from Kimberly-Clark Corporation under marks such as Spunguard® and Evolution®. The spunbonded layers on the SMS laminates provide durability and the internal meltblown barrier layer provides porosity and additional clothlike feel. Similar to an SMS laminate, an SM laminate is a spunbond layer laminated to a meltblown layer.

The articles 10 may include one or more elastic components for providing various desired characteristics. The materials can contain elastic strands or sections uniformly or randomly distributed throughout the material. Alternatively, the elastic component can be an elastic film or an elastic nonwoven web. In general, any material known in the art to possess elastomeric characteristics can be used in the present invention as an elastomeric component. Useful elastomeric materials can include, but are not limited to, films, foams, nonwoven materials, etc.

Other exemplary elastomeric materials which may be used include polyurethane elastomeric materials such as, for example, those available under the trademark ESTANE® from B.F. Goodrich & Co. or MORTHANE® from Morton Thiokol Corp., polyester elastomeric materials such as, for example, those available under the trade designation HYTREL® from E.I. DuPont De Nemours & Company, and those known as ARNITEL®, formerly available from Akzo Plastics of Amhem, Holland and now available from DSM of Sittard, Holland.

Another suitable material is a polyester block amide copolymer. Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

When incorporating an elastomeric component, such as described above, into a base web of the present invention, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck-bonded laminates.

The elastic member used in neck-bonded materials, stretch-bonded materials, stretch-bonded laminates, neck-bonded laminates and in other similar laminates can be made from materials, such as described above, that are formed into films, such as a microporous film, fibrous webs, such as a web made from meltblown fibers, spunbond filaments or foams. A film, for example, can be formed by extruding a filled elastomeric polymer and subsequently stretching it to render it microporous.

In one embodiment, the elastic member can be a neck stretched bonded laminate. As used herein, a neck stretched bonded laminate is defined as a laminate made from the combination of a neck-bonded laminate and a stretch-bonded laminate. Examples of necked stretched bonded laminates are disclosed in U.S. Pat. Nos. 5,114,781 and 5,116,662, which are both incorporated herein by reference. Of particular advantage, a neck stretch bonded laminate is stretchable in the machine direction and in a cross machine direction. Further, a neck stretch-bonded laminate can be made with a nonwoven basing that is texturized. In particular, the neck stretched bonded laminate can be made so as to include a nonwoven facing that gathers and becomes bunched so as to form a textured surface. In this manner, the neck stretched bonded laminate can be used to form the entire finger wipe having stretch characteristics in two directions and having a textured surface for cleaning the teeth and gums of a user.

As mentioned, the functional element may be a fluid composition intended to be applied or used by the article 10. Examples of such compositions include, but are not limited to, medications, lotions, diaper rash ointments, alcohols, oral anesthetics, facial make-up removal agents, cleaning agents, polishing agents, and the like.

Certain compositions and additives are used when the article is a finger wipe intended as an oral cleaning device. Examples of such dental agents include, but are not limited to alginates, soluble calcium salts, phosphates, flourides, such as sodium flouride (NaF) or stannous flouride (SnF 2), and the like. Moreover, mint oils and mint oil mixtures can be applied to a finger wipe of the present invention. For instance, in one embodiment, peppermint oil can be applied to the finger wipe. Moreover, in another embodiment, a mint oil/ethanol mixture can be applied. Components of mint oil (e.g., menthol, carvone) can also be used. Additionally, various whitening agents can be applied to the finger wipe. Examples of whitening agents include peroxides and in situ sources of peroxide, such as carbamide peroxide.

Furthermore, in some embodiments, the finger wipe can also comprise an anti-ulcer component. In particular, one embodiment of the present invention can comprise a component designed to act as an anti-H. pylori agent. In general, any additive known in the art to be an anti-ulcer or anti-H. pylon agent can be used in the present invention. In one embodiment, for example, bismuth salts can be utilized. One particularly effective bismuth salt, bismuth subcitrate, is described in more detail in U.S. Pat. No. 5,834,002 to Athanikar, which is incorporated herein in its entirety by reference thereto. Another example of a suitable bismuth salt is PEPTO-BISMOL sold by The Procter & Gamble Company, containing bismuth subsalicylate. In addition to bismuth salts, other examples of suitable anti-ulcer additives include, but are not limited to, tetracycline, erythromycin, clorithromycin or other antibiotics. Furthermore, any additive useful for treating peptic ulcers, such as H2-blockers, omeprazole, sucralfate, and metronidazole, can be used as well.

Other additives and compositions can include, but are not limited to, flavoring agents, anti-microbial agents, preservatives, polishing agents, hemostatic agents, surfactants, etc. Examples of suitable flavoring agents include various sugars, breath freshening agents, and artificial sweeteners as well as natural flavorants, such as cinnamon, vanilla and citrus. Moreover, in one embodiment, xylitol, which provides a cooling effect upon dissolution in the mouth and is anti-cariogenic, can be used as the flavoring agent. As stated, preservatives, such as methyl benzoate or methyl paraben, can also be applied to a finger wipe of the present invention. The additives can be applied to the finger wipe as is or they can be encapsulated in order to preserve the additives and/or to provide the additive with time release properties.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A disposable absorbent article worn by a user for absorbing bodily fluids, wherein said article is one of a diaper, training pant, adult incontinent article, or child's swim pant, comprising:
   a liquid permeable cover layer, a liquid impermeable baffle, and an absorbent structure disposed between said cover layer and said baffle,
   an attachment structure configured to secure said article relative to said user, said attachment structure further comprising
   attachment tabs disposed on opposite lateral sides of said absorbent article, said attachment tabs comprising a web of hook material having individual hooks and an outer material overlying in said hook material and having a plurality of slits defined completely through the outer material along the surface thereof, said slits configured such that upon stretching of said tabs, said slits part to expose said individual hooks through said outer material, said hooks securing to a complimentary material on said absorbent article to secure said absorbent article to the user.

2. A disposable feminine hygiene article, comprising a liquid permeable cover layer, a liquid impermeable baffle, and an absorbent structure disposed between said cover layer and said baffle, and an attachment structure disposed on said baffle so as to attach said feminine hygiene article to the user's under garment, said attachment structure further comprising a web of hook material having individual hooks and an outer material overlying said hook material and having a plurality of slits defined completely through the outer material along the surface thereof, said slits configured such that upon stretching of said baffle, said slits part to expose said individual hooks through said outer material, said hooks securing to a complimentary material on the user's undergarment.

3. A disposable garment comprising a securement device configured to tighten a portion of said garment on a user, said securement device further comprising:

a web of hook material having individual hooks;

an outer material layer overlying said hook material, said outer material layer further comprising a plurality of slits defined completely through said outer material layer along the surface thereof, said slits configured such that upon stretching of said outer material layer, said slits part to expose said individual hooks through said outer material layer.

4. The disposable garment as in claim 3, wherein said securement device comprises a strap configured to be pulled and attached to a portion of said garment.

5. The disposable garment as in claim 3, wherein said garment is a disposable surgical gown.

* * * * *